United States Patent [19]

Murib et al.

[11] Patent Number: 4,550,181

[45] Date of Patent: Oct. 29, 1985

[54] PROCESS FOR PREPARING GAMMA-CAPROLACTONE FROM POLYCAPROLACTONE

[75] Inventors: Jawad H. Murib, Cincinnati; John H. Kahn, Wyoming, both of Ohio

[73] Assignee: National Distillers and Chemical Corporation, New York, N.Y.

[21] Appl. No.: 624,308

[22] Filed: Jun. 25, 1984

[51] Int. Cl.$^4$ .......................................... C07D 307/32
[52] U.S. Cl. .................................................. 549/326
[58] Field of Search ........................................ 549/326

[56] References Cited

U.S. PATENT DOCUMENTS 3,935,235  1/1976  Hardy et al. .................... 549/326

*Primary Examiner*—Jane T. Fan
*Attorney, Agent, or Firm*—Kenneth D. Tremain

[57] ABSTRACT

A process for preparing gamma-caprolactone comprising heating polycaprolactone in the presence of catalytically effective amounts of an acid comprised of hydrogen halides in a water solution to a temperature in the range of about 175° C. to about 275° C. and the ratio of water to polycaprolactone is in the range of about 1:1 to about 10:1.

22 Claims, No Drawings

PROCESS FOR PREPARING GAMMA-CAPROLACTONE FROM POLYCAPROLACTONE

FIELD OF THE INVENTION

This invention relates to a process for the production of lactones and more particularly to a process for the production of gamma-caprolactone.

BACKGROUND OF THE INVENTION

Gamma-caprolactone is commercially and industrially attractive because of its use as a flavor additive in foods and tobacco and for its potential as an intermediate for insecticides.

Gamma-caprolactone (γ-caprolactone) has the structure:

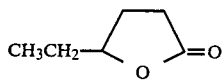

Gamma-caprolactone is also known as 4-hexalactone and 4-ethyl butyrolactone and in Chemical Abstracts, it is identified as 5-Ethyldihydro-2 (3H) furanone with a registry number of 695-06-7.

Various prior art methods exist for the production of gamma-caprolactone, but these methods are either expensive or do not produce good yields.

For example, U.S. Pat. No. 3,935,235 to Hardy, et al. discloses a multi-step process for the production of gamma-caprolactone. According to the process of Hardy, et al., a feed-material containing the group —O—$(CR_2)_n$—CO— in which R represents a hydrogen atom or a methyl-group and n is an integer from 5 to 11 in a macrocyclic ring or an acyclic chain, is heated to temperatures of from 300° to 500° C. to form a mono unsaturated acyclic carboxylic acid. The mono unsaturated acyclic carboxylic acid is separated and subjected to cyclising by contacting it with a catalyst comprising a strong protonating agent such as sulfuric acid, toluenesulphonic acid, formic acid, oxalic acid, trifluoroacetic acid, a cation exchange resin in the free-acid form, a strongly acidic mixture containing hydrogen ions such as hydrogen halides in acetic acid or similar strong protonating agents.

The Hardy, et al. process disadvantageously requires a two-step reaction as well as an intermediate separation step to produce gamma-caprolactone. Further, the Hardy, et al. process requires high temperatures (at least 300° C.) to perform the first step of its process.

SUMMARY OF THE INVENTION

It is therefore an object of the present invention to provide a one-step process for the economical production of gamma-caprolactone utilizing relatively mild reaction conditions.

To achieve the objects in accordance with the purposes of the invention, as embodied and broadly described herein, the invention comprises a process for preparing gamma-caprolactone comprising heating polycaprolactone in the presence of catalytically effective amount of a hydrogen halide in a water solution at a temperature in the range of about 175° C. to about 275° C. In preferred embodiments of the invention, the catalyst is hydriodic acid.

DETAILED DESCRIPTION OF THE INVENTION

In accordance with the present invention, it has unexpectedly been found that gamma-caprolactone is prepared in yields of 25% or more by heating polycaprolactone in the presence of catalytically effective amounts of aqueous solutions of hydrogen halides, which acids serve as protonating catalysts for the reaction.

The aqueous hydrogen halide solutions of the present invention generally have a mole ratio of water to polycaprolactone of at least about 1:1. Preferably, the mole ratio of water to polycaprolactone is about 1:1 to about 10:1.

For the purposes herein, catalytically effective amounts of the aqueous hydrogen halide have been found to be, for example, in a mole ratio range of polycaprolactone to hydrogen halide of about 5:1 to about 60:1, respectively. This range can vary considerably and the amount of hydrogen halide catalyst present may be outside this range and still produce gamma-caprolactone in accordance with the process of the invention although this mole ratio range of hydrogen halide has been found to effectively produce gamma-caprolactone.

The hydriodic or hydrobromic acid catalyst can optionally be promoted with a catalyst-promoting effective amount of a Group VIII metal. In preferred embodiments, the catalyst promoter is ruthenium on carbon which may act to increase the reaction rate to produce the gamma-caprolactone.

Hydriodic and hydrobromic acid are the preferred protonating catalyst.

The reaction is carried out in a temperature range of about 175° C. to about 275° C. Preferably, the temperature range of the reaction is about 200° C. to about 225° C. and more preferably the temperature is about 200° C. The temperature of the reaction may vary greatly and even exceed the range specified to produce gamma-caprolactone. Generally, the reaction is carried out at atmospheric pressure but may be carried out under an inert gas such as $N_2$ or $CO_2$.

A reaction time of 6 hours has been found to be sufficient for producing gamma-caprolactone on the scale of reactions utilized in the present example hereinafter detailed. Reaction times may vary as quantities of reactants used and reaction conditions vary, as would be known to those skilled in the art.

The invention will now be illustrated by examples. The examples are not intended to be limiting of the scope of the present invention, but in conjunction with the general and detailed description above, the example provide further understanding of the present invention and outline further embodiments of the process of the invention.

The general scheme of reaction can be illustrated as follows:

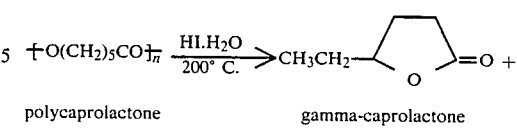

polycaprolactone          gamma-caprolactone

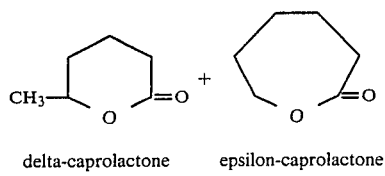

delta-caprolactone    epsilon-caprolactone

The starting materials, solvents, and reagents utilized in the examples whose method of preparation are not indicated, are commercially available compounds which would be available from chemical supply houses well known to the art.

EXAMPLE 1

A 71 ml Hastelloy pressure reactor with glass liner was charged with 5 g (44 mM) commercial polycaprolactone pellets, 5 ml (277 mM) water and 1 ml (6.5 mM) 57% aqueous hydriodic acid. The mixture was flushed with $N_2$ to displace any $O_2$, sealed and heated with shaking in an oven at 200° C. for six hours. The reaction mixture contained 1.27 g (11 mM) gamma-caprolactone, 0.2 g delta-caprolactone and 0.3 g epsilon-caprolactone as analyzed by gas chromatography and confirmed by mass spectrometry. The gamma-caprolactone yield was 25% based on the initial weight of polycaprolactone charged to the reactor.

Separation of gamma-caprolactone from $H_2O$ to the extent of 97% was achieved by phase separation and chloroform extraction of the water layer.

EXAMPLE 2

The procedure of Example 1 is repeated except that the charge also contains 0.5 g 5% Ru/C. The reaction mixture contains gamma-caprolactone.

EXAMPLE 3

The procedure of Example 1 is repeated except that HBr is used as the catalyst at a temperature of 225° C. The reaction mixture contains gamma-caprolactone.

EXAMPLE 4

The procedure of Example 1 is repeated except that 1 ml of concentrated hydrochloric acid (12 mM) is used in place of hydriodic acid at a temperature of 250° C. The reaction mixture contains gamma-caprolactone.

The scope of the present invention is not limited by the description, examples, and suggestions used herein, and modifications can be made without departing from the spirit of the invention. Thus, it is intended that the present invention cover the modifications and variations of this invention provided they come within the scope of the appended claims and their equivalents.

What is claimed is:

1. A process for preparing gamma-caprolactone comprising heating polycaprolactone in the presence of catalytically effective amounts of an acid comprised of a hydrogen halide in a water solution at a temperature in the range of about 175° C. to about 275° C.

2. The process for preparing gamma-caprolactone comprising heating polycaprolactone in the presence of catalytically effective amounts of an acid in water solvent wherein the acid is selected from the group consisting of hydriodic acid, hydrobromic acid, hydrochloric acid, and mixtures thereof to a temperature in the range of about 175° C. to about 275° C.

3. The process of claim 2 wherein the acid is hydriodic acid.

4. The process of claim 1 wherein the reaction is conducted at a temperature in the range of about 200° C. to about 225° C.

5. The process of claim 2 wherein the reaction is conducted at a temperature in the range of about 200° C. to about 225° C.

6. The process of claim 3 wherein the reaction is conducted at a temperature in the range of about 200° C. to about 225° C.

7. The process of claim 1 wherein the reaction is conducted at a temperature of about 200° C.

8. The process of claim 2 wherein the reaction is conducted at a temperature of about 200° C.

9. The process of claim 3 wherein the reaction is conducted at a temperature of about 200° C.

10. The process of claim 1 wherein the mole ratio of water to polycaprolactone is at least about 1:1.

11. The process of claim 2 wherein the mole ratio of water to polycaprolactone is at least about 1:1.

12. The process of claim 3 wherein the mole ratio of water to polycaprolactone is at least about 1:1.

13. The process of claim 1 wherein the mole ratio of water to polycaprolactone is in the range of about 1:1 to about 10:1.

14. The process of claim 2 wherein the mole ratio of water to polycaprolactone is in the range of about 1:1 to about 10:1.

15. The process of claim 3 wherein the mole ratio of water to polycaprolactone is in the range of about 1:1 to about 10:1.

16. The processs according to claim 1 wherein the acid catalyst is promoted with a catalyst-promoting effective amount of a Group VIII metal.

17. The process according to claim 16 wherein the Group VIII metal is ruthenium.

18. The process according to claim 17 wherein the ruthenium is supported on carbon.

19. A process for preparing gamma-caprolactone comprising heating polycaprolactone in the presence of catalytically effective amounts of an acid in water solvent wherein the acid is selected from the group consisting of hydriodic acid, hydrobromic acid, hydrochloric, and mixtures thereof to a temperature in the range of about 200° C. to about 225° C., wherein the mole ratio of water to polycaprolactone is in the range of about 1:1 to about 10:1.

20. The process according to claim 19 wherein the acid catalyst is promoted with a catalyst-promoting effective amount of ruthenium metal on a carbon support.

21. A process for preparing gamma-caprolactone comprising heating polycaprolactone in the presence of an aqueous solution of hydriodic acid to a temperature of about 200° C. and the mole ratio of water to polycaprolactone is in the range of from about 1:1 to about 10:1.

22. The process according to claim 21 wherein the hydriodic acid is promoted with a catalyst-promoting effective amount of ruthenium metal on a carbon support.

* * * * *